United States Patent
Stadler et al.

(10) Patent No.: US 8,750,976 B2
(45) Date of Patent: Jun. 10, 2014

(54) IMPLANTED MULTICHAMBER CARDIAC DEVICE WITH SELECTIVE USE OF RELIABLE ATRIAL INFORMATION

(75) Inventors: Robert W. Stadler, Shoreview, MN (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 518 days.

(21) Appl. No.: 13/038,664

(22) Filed: Mar. 2, 2011

(65) Prior Publication Data

US 2012/0226179 A1    Sep. 6, 2012

(51) Int. Cl.
*A61B 5/04*    (2006.01)
*A61N 1/00*    (2006.01)

(52) U.S. Cl.
USPC .......................... 600/515; 600/516; 607/119

(58) Field of Classification Search
USPC ................... 600/515–516; 607/119
See application file for complete search history.

(56) References Cited

U.S. PATENT DOCUMENTS

| | | | |
|---|---|---|---|
| 6,112,119 A | 8/2000 | Schuelke | |
| 6,351,675 B1 | 2/2002 | Tholen | |
| 6,393,316 B1 | 5/2002 | Gillberg | |
| 6,512,946 B1 | 1/2003 | Hahn | |
| 6,917,830 B2 | 7/2005 | Palreddy | |
| 7,065,398 B2 | 6/2006 | Hettrick | |
| 7,580,740 B2 | 8/2009 | Kim | |
| 7,797,037 B2 | 9/2010 | Elahi | |
| 8,280,509 B2 * | 10/2012 | Sathaye | 607/9 |
| 2003/0204215 A1 | 10/2003 | Gunderson | |
| 2007/0135863 A1 | 6/2007 | Gunderson | |
| 2010/0274148 A1 | 10/2010 | Zhang | |

OTHER PUBLICATIONS (PCT/US2012/021534) PCT Notification of Transmittal of the International Search Report and the Written Opinion of the International Searching Authority.

* cited by examiner

*Primary Examiner* — Nicole F Lavert
(74) *Attorney, Agent, or Firm* — Michael C. Soldner (57) ABSTRACT

An implantable medical device acquires a first cardiac signal in a first heart chamber and a second cardiac signal in a second heart chamber. The device determines if the first signal is unreliable. In response to determining the first signal to be unreliable, the device switches from a first cardiac arrhythmia detection mode of operation to a second cardiac arrhythmia detection mode of operation, the first detection mode requiring the use of both the first cardiac signal and the second cardiac signal and the second detection mode requiring the use of the second cardiac signal and not requiring the use of the first cardiac signal.

21 Claims, 6 Drawing Sheets

IMPLANTED MULTICHAMBER CARDIAC DEVICE WITH SELECTIVE USE OF RELIABLE ATRIAL INFORMATION

TECHNICAL FIELD

The present disclosure relates generally to implantable medical devices and, in particular, to a device and method for detecting cardiac events selectively using atrial information.

BACKGROUND

Clinical evidence has shown that implantable cardioverter defibrillators (ICDs) reduce mortality, which has led to a significant increase in their use. Patients implanted with an ICD, however, potentially face the problem of defibrillator shocks delivered unnecessarily for rhythms other than ventricular fibrillation (VF) or sustained ventricular tachycardia (VT). Unnecessary ICD shocks cause undue pain, psychological disturbance and can potentially induce more serious arrhythmias in some patients. If supraventricular tachycardia (SVT), including atrial fibrillation, atrial tachycardia and sinus tachycardia, are incorrectly detected as VT, ventricular therapy may be delivered unnecessarily. Therefore, appropriately distinguishing SVT from VT may help to reduce the incidence of unnecessary shocks, without decreasing ICD efficacy.

For implanted cardiac devices, the electrical activity of the atria can provide valuable information to aid in appropriate rhythm discrimination and therapy delivery. For example, discriminators of SVT from VT can make use of intervals between P-waves associated with atrial depolarizations and R-waves associated with ventricular depolarizations. These intervals may be measured from intracardiac EGM signals as P-R intervals or R-P intervals and such intervals, along with patterns of sensed P-waves and R-waves, can be used in distinguishing between SVT and VT. The atrial electrical activity information, however, can at times be unreliable because of noise corruption, very small P-wave signal amplitude, the confounding presence of ventricular electrical activity appearing as far-field signals on an atrial signal, and dislodgement of the atrial lead.

DETAILED DESCRIPTION

In the following description, references are made to illustrative embodiments. It is understood that other embodiments may be utilized without departing from the scope of the disclosure.

The proper use of atrial information can improve cardiac rhythm discrimination and therapy delivery in implanted cardiac devices. An atrial EGM signal, however, can at times be unreliable due to undersensing of atrial P-waves, non-physiological artifact in the atrial signal, oversensing of far-field R-waves, or atrial lead dislodgement into the ventricle. These periods of unreliable atrial information may adversely affect cardiac device performance in properly discriminating rhythms and selecting the best possible therapy to deliver to the patient's heart. When the atrial signal information is unreliable, the cardiac device may perform superiorly if behaving as a single chamber (ventricular) only device. A dual- or multi-chamber implanted cardiac device that makes proper use of atrial information when it is reliable, and ignores the atrial information when it is not reliable, could dramatically improve overall system performance. Clinical benefits may include reduction of inappropriate cardioversion/defibrillation (CV/DF) shocks, promoting proper delivery of CV/DF shocks during true VT//VF, and improved pacing and cardiac resynchronization therapies.

Figure 1:
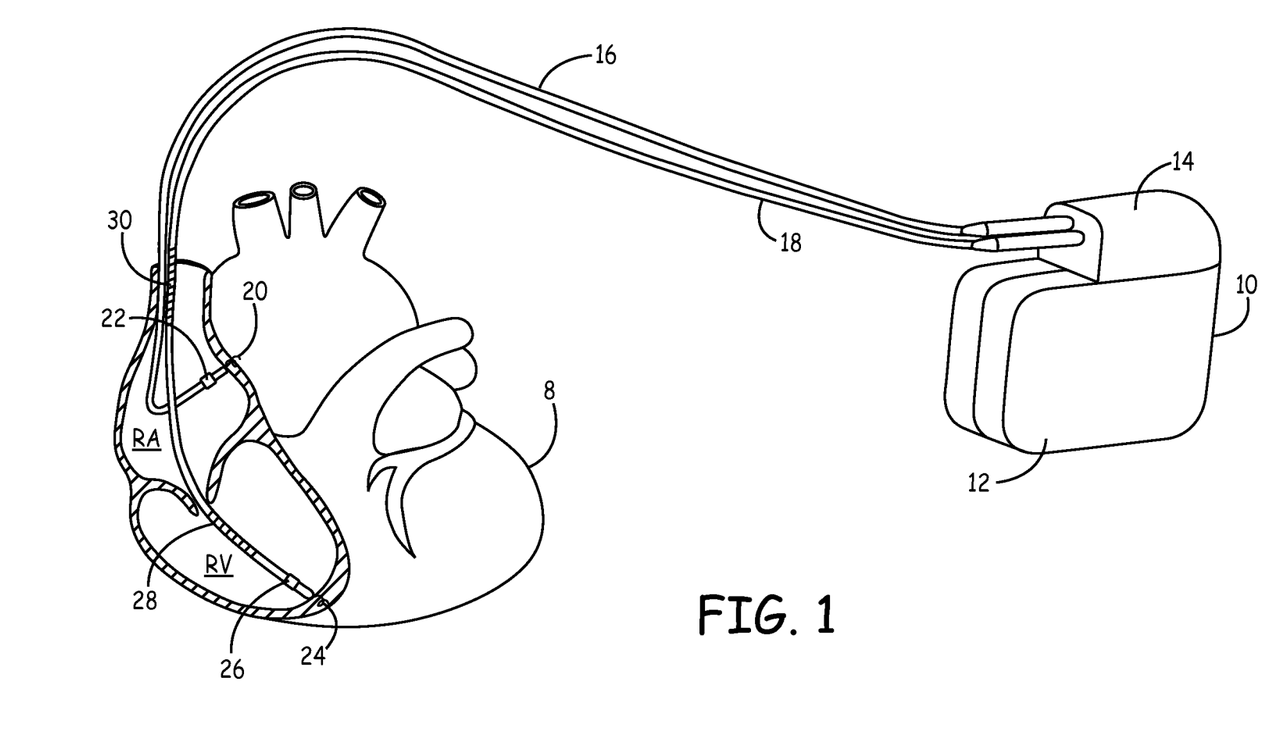
FIG. 1 is a schematic diagram of one embodiment of an implantable medical device (IMD) coupled to a patient's heart by a right atrial lead and a right ventricular lead.

FIG. 1 is a schematic diagram of one embodiment of an IMD 10 coupled to a patient's heart 8 by a right atrial lead 16 and a right ventricular lead 18. IMD 10 is shown embodied as an ICD, but may alternatively be embodied as any implantable cardiac monitoring device including a cardiac pacemaker or cardiac monitor, that utilizes atrial and ventricular electrical signals for detecting cardiac events or arrhythmias such as VT, VF and SVT. IMD 10 is provided for sensing intrinsic heart activity, detecting cardiac arrhythmias, and delivering cardiac stimulation pulses, as appropriate, to one or more heart chambers in response to detecting an arrhythmia.

The heart is shown in a partially cut-away view illustrating an upper heart chamber, the right atrium (RA), and a lower heart chamber, the right ventricle (RV). Leads 16 and 18 respectively connect IMD 10 with the RA and the RV. A remote indifferent can electrode is formed as part of the outer surface of the IMD housing 12.

RA lead 16 is passed through a vein into the RA chamber. RA lead 16 is formed with a connector fitting into a connector bore of the IMD connector block 14 for electrically coupling a RA tip electrode 20 and RA ring electrode 22 to IMD internal circuitry via insulated conductors extending within the body of lead 16. RA tip electrode 20 and RA ring electrode 22 may be used for acquiring a RA intracardiac electrogram (EGM) signal, also referred to herein as an "atrial electrical signal" or simply "atrial signal". Electrodes 20 and 22 may also be used for delivering cardiac pacing pulses in the RA during a pacing therapy that includes atrial pacing.

RV lead 18 is passed through the RA into the RV. The RV lead distal end carries RV tip electrode 24 and RV ring electrode 26 used for acquiring a RV EGM signal, also referred to herein as a "ventricular electrical signal" or simply "ventricular signal". Electrodes 24 and 26 may also be used in delivering RV pacing pulses, e.g. during bradycardia pacing, cardiac resynchronization therapy, or anti-tachycardia pacing therapy. RV lead 18 also carries an RV coil electrode 28 and a superior vena cava (SVC) coil electrode 30 for use in delivering high voltage cardioversion/defibrillation shocks. RV lead 18 is formed with a proximal connector fitting into a corresponding connector bore of the IMD connector block 14 for electrically coupling electrodes 24, 26, 28 and 30 to IMD internal circuitry.

The electrodes 20, 22, 24, 26, 28 and 30 and the remote can electrode formed along housing 12 can be selectively employed to provide a number of unipolar and bipolar electrode combinations for acquiring atrial and ventricular signals and for delivering electrical pulses to the heart 8. While a particular IMD and associated leads and electrodes are illustrated in FIG. 1, numerous implantable device configurations are possible that include at least one electrode pair for obtaining atrial signals and at least one electrode pair for obtaining ventricular signals. Such electrodes may be any combination of lead-based or leadless electrodes, including transvenous, subcutaneous, endocardial, epicardial, or transcutaneous electrodes.

IMD 10 is shown as a dual-chamber device capable of sensing and stimulation in an upper RA chamber and a lower RV chamber. It is understood that IMD 10 may be modified to operate as a single chamber device or bi-ventricular device for delivering ventricular therapies to one or both ventricular chambers with multi-chamber sensing in three or even all four heart chambers. In some embodiments, a coronary sinus lead may extend from the IMD into the coronary sinus and further into a cardiac vein to position one or more electrodes for sensing and pacing in the left ventricle. A coronary sinus lead may include one or more electrodes positioned adjacent to the left atrium for pacing and sensing in the left atrium. Furthermore, it is recognized that embodiments may be practiced in a single chamber, dual chamber or multi-chamber implantable cardiac device that does not include cardioversion and defibrillation functions.

It is further contemplated that electrodes carried by leads 16, 18 and IMD housing 12 may be used for measuring impedance signals to obtain information relating to atrial and ventricular activation. Leads 16, 18 and IMD housing 12 may further include other sensors besides electrodes for acquiring cardiac signals and sensing cardiac events. Other sensors may include a pressure sensor, accelerometer, optical sensor, and acoustical sensor. Any of these sensors producing a cyclical signal corresponding to activation of an atrial or ventricular heart chamber may be used in detecting cardiac events.

Figure 2:
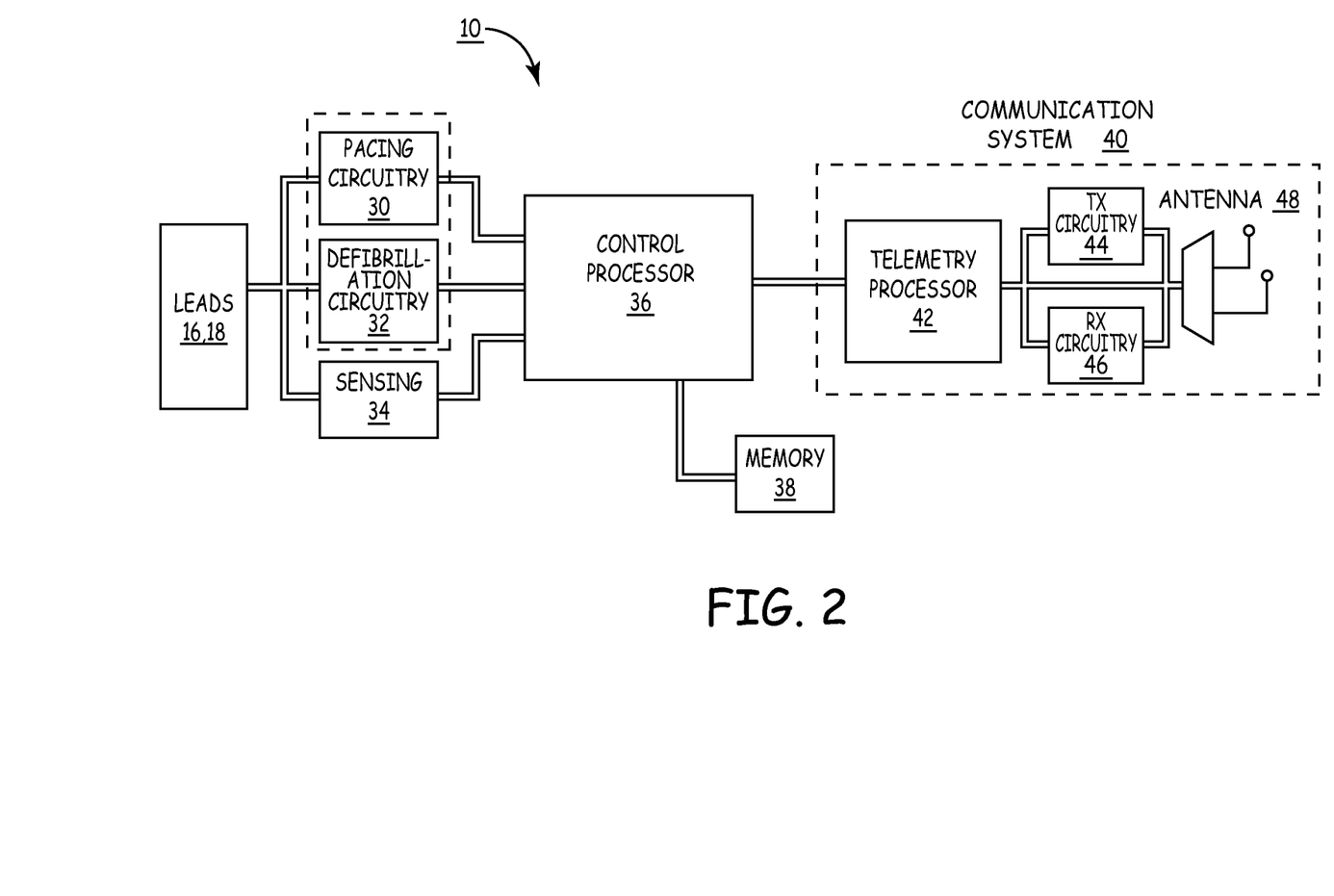
FIG. 2 is a functional block diagram of an IMD according to one embodiment.

FIG. 2 is a functional block diagram of IMD 10 according to one embodiment. Circuitry located within the housing 12 of IMD 10 of FIG. 1, includes pacing circuitry 30, defibrillation circuitry 32, sensing circuitry 34, control processor 36, memory 38, and communication system 40. Leads 16 and 18 are connected to pacing circuitry 30, defibrillation circuitry 32 and sensing circuitry 34. The internal circuitry of IMD 10 may be implemented using any combination of an application specific integrated circuit (ASIC), an electronic circuit, a processor (shared, dedicated, or group) and memory that execute one or more software or firmware programs, a combinational logic circuit, state machine, or other suitable components that provide the described functionality. Each lead (and in turn individual electrodes associated with each lead) coupled to the IMD 10 may be used in multiple capacities to sense cardiac signals (e.g. P-waves and R-waves), deliver pacing pulses, and deliver cardioversion/defibrillation shocks.

Control processor 36 receives atrial and ventricular signal input through sensing circuitry 34 from leads 16 and 18 and acquired by the electrodes connected to leads 16 and 18. Based on input received from sensing circuitry 34, control processor 36 performs an arrhythmia detection algorithm for detecting arrhythmias and selecting a therapy as needed. Therapy may include providing anti-tachycardia pacing (ATP) therapy using pacing circuitry 30 and selected pacing electrodes, providing defibrillation or cardioversion shocks using defibrillation circuitry 32 and a high voltage coil electrode 28, 30.

Control processor 36 stores selected cardiac signal data to memory 38, and retrieves stored data from memory 38 as necessary in performing detection and therapy delivery algorithms and further stores data relating to detected arrhythmia episodes. Communication system 40 includes telemetry processor 42, transmission circuitry 44, receiving circuitry 46, and antenna 48. Communication system 40 allows communication between IMD 10 and devices external to the patient for programming IMD 10 and retrieving data stored in memory 38.

Control processor 36 is configured to receive atrial and ventricular cardiac signal information from sensing circuitry 34 and execute detection algorithms programmed into IMD 10 for detecting and discriminating cardiac events. In particular, control processor 36 uses atrial signals and ventricular signals to discriminate SVT (including atrial flutter, atrial fibrillation, atrial tachycardia and sinus tachycardia) from VT and VF. Control processor 36 is further configured to determine if the atrial signal is unreliable for cardiac event detection. In response to determining that the atrial signal is unreliable, the control processor 36 changes the cardiac event detection algorithm to eliminate the use of the unreliable atrial signal information. The detection algorithm is switched to an algorithm that relies on ventricular signal information without requiring the use of atrial signal information. If the atrial signal is determined to be reliable again, the cardiac event detection algorithm is changed again to restore the use of both atrial and ventricular signal information.

Figure 3:
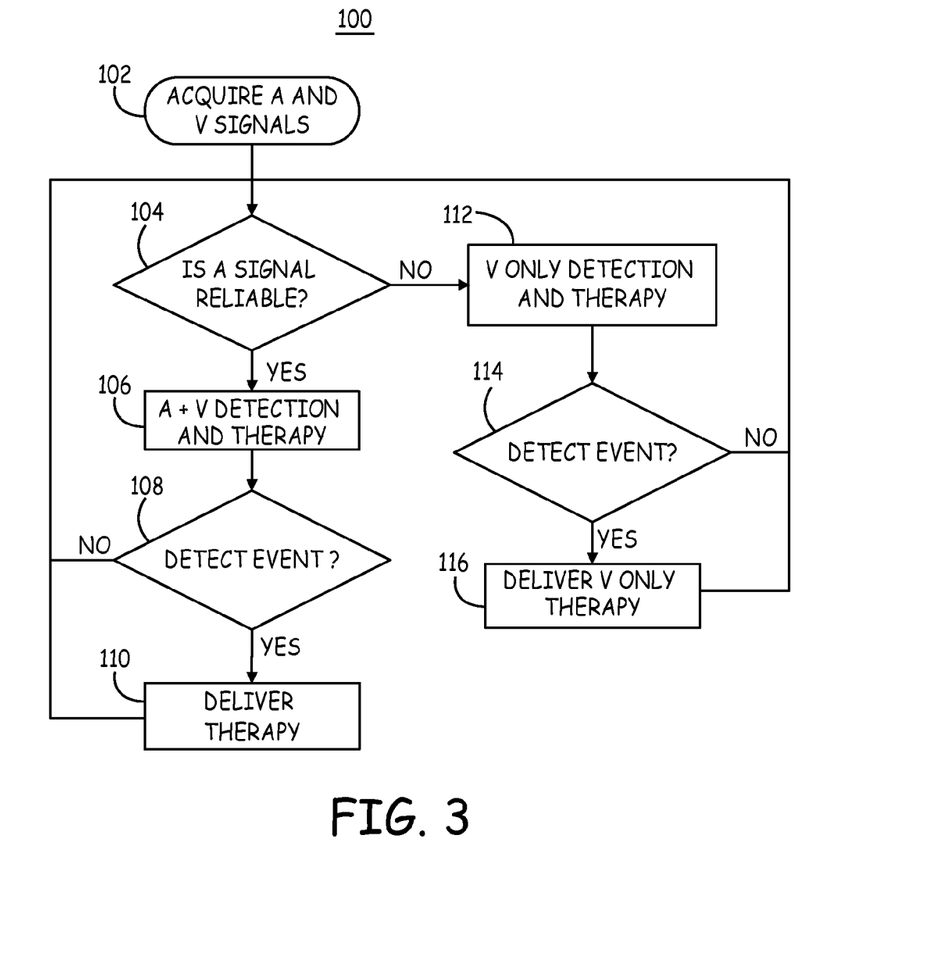
FIG. 3 is a flow chart of one method for controlling cardiac arrhythmia detection in an IMD.

FIG. 3 is a flow chart 100 of one method for controlling cardiac event detection in an IMD. Flow chart 100 and other flow charts presented herein are intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102 both an atrial signal and ventricular signal are acquired by IMD sensing circuitry. In a dual chamber device, one atrial signal and one ventricular signal are acquired. In multi-chamber devices, more than one atrial signal and more than one ventricular signal may be acquired depending on the electrodes available and the particular cardiac event detection algorithms employed.

The illustrative embodiments described herein relate to the use of electrical signals of the heart, in particular an atrial EGM signal and a ventricular EGM signal. In alternative embodiments, an atrial signal and/or a ventricular signal may be acquired using other types of sensors such as a pressure sensor, an impedance sensor, an accelerometer or other sensor producing a signal correlated to the cyclical electrical or mechanical activation of the corresponding heart chamber. For example, a sensing threshold could be applied to an atrial pressure signal used for sensing atrial activations and another sensing threshold could be applied to a ventricular pressure signal used for sensing ventricular activations. The methods for determining if an atrial signal is reliable for use in cardiac event detection and a cardiac event detection algorithm itself may be applied to any atrial signal correlated to the cyclical function of the atria. An atrial signal may be obtained using sensors other than electrodes, such as a mechanical, optical, acoustical, or other type of sensor.

At block 104, the atrial signal is monitored by the IMD control processor to determine if it is unreliable for use in detecting or discriminating arrhythmias. Methods that may be used for determining that the atrial signal is unreliable will be described in greater detail in conjunction with FIGS. 4 and 6. If the atrial signal is found to be reliable at decision block 104, the IMD operates in a dual (or multi-) chamber mode. The use of both the atrial and ventricular signals for cardiac event detection according to detection algorithms implemented in the IMD is enabled at block 106. Atrial, ventricular, and dual chamber therapies are enabled at block 106 according to programmed therapies, which may include pacing, ATP, CV/DF shocks, cardiac resynchronization therapy and so on.

At block 108, programmed cardiac event detection algorithms operate using both the atrial signal and ventricular signal as input. For example, sensed P-wave signals may be used to compare atrial and ventricular rates, determine 1:1 correspondence or other patterns of atrial and ventricular sensed events, and for P-wave morphology analysis. This information may be used in a detection algorithm used to discriminate SVT from VT/VF.

If a cardiac event is detected, which may be a supraventricular event, a ventricular event, or a dual chamber event, a therapy may be delivered in the atrial, ventricular or both upper and lower chambers according to a programmed menu of therapies at block 110. If no event is detected requiring therapy, the process returns to block 104 and continues monitoring the atrial signal.

If the atrial signal is found to be unreliable at decision block 104, the IMD switches to a single chamber mode of operation for arrhythmia detection and optionally a single (or bi-) chamber mode of therapy delivery. At block 112, the arrhythmia detection algorithm is switched to an algorithm that requires only ventricular signal input. Atrial signal information is ignored. Likewise, any atrial (or dual-chamber) therapies that are programmed in the IMD may be disabled or withheld until the atrial signal is found to be reliable again.

As long as no arrhythmic event is detected at block 114, the process returns to block 104 to continue monitoring the atrial signal. If the atrial signal becomes reliable again, the dual- or multi-chamber mode of arrhythmia detection and therapy delivery may be restored. The atrial signal may be monitored at block 104 on a beat-by-beat basis such that the detection algorithm may be switched between a ventricular-only detection algorithm and an atrial plus ventricular detection algorithm on a beat-by-beat basis.

Alternatively, atrial signal monitoring may occur on a beat-by-beat basis but switching of the detection mode of the IMD may be performed on a less frequent basis. For example, if the atrial signal is found unreliable, the ventricular-only event detection enabled at block 112 may be maintained for a predetermined number of cardiac cycles. At the end of the predetermined number of cardiac cycles, the event detection may switch back to a detection algorithm that uses atrial information if the atrial signal has again been found to be reliable. In still other embodiments, if a detection algorithm that utilizes atrial signal information has been disabled for a period of time (or predetermined number of cardiac cycles), the atrial signal may not be rechecked at block 104 until the expiration of the disabled time period or until manually re-enabled.

If a cardiac event is detected at block 114 using only ventricular signal information, a therapy is delivered at block 116. When VT/VF detection using only a ventricular signal is enabled, only ventricular therapies may be delivered at block 116 according to a programmed menu of therapies. Alternatively, if discrimination of SVT and VT/VF is performed using an algorithm that requires only a ventricular signal (which may include one or more ventricular signals acquired using one or more ventricular sensing vectors), therapies delivered at block 116 may include an atrial therapy when an SVT or dual chamber event is detected.

After delivering therapy, the process returns to block 104 to continue monitoring the atrial signal. In some embodiments, if a detection algorithm that utilizes atrial signal information has been disabled for a predetermined period of time, a therapy delivery may trigger a re-analysis of the atrial signal, even if the time period has not expired, in order to restore the use of atrial signal information as quickly as possible.

Switching the cardiac event detection mode of operation from one that uses both atrial and ventricular signal information (block 106) to one that uses ventricular information but not atrial information may involve selecting an entirely different algorithm, enabling or disabling a criterion within a detection algorithm that relates to atrial information, or enabling or disabling a more complicated detection algorithm component that relies only on the ventricular signal.

Figure 4:
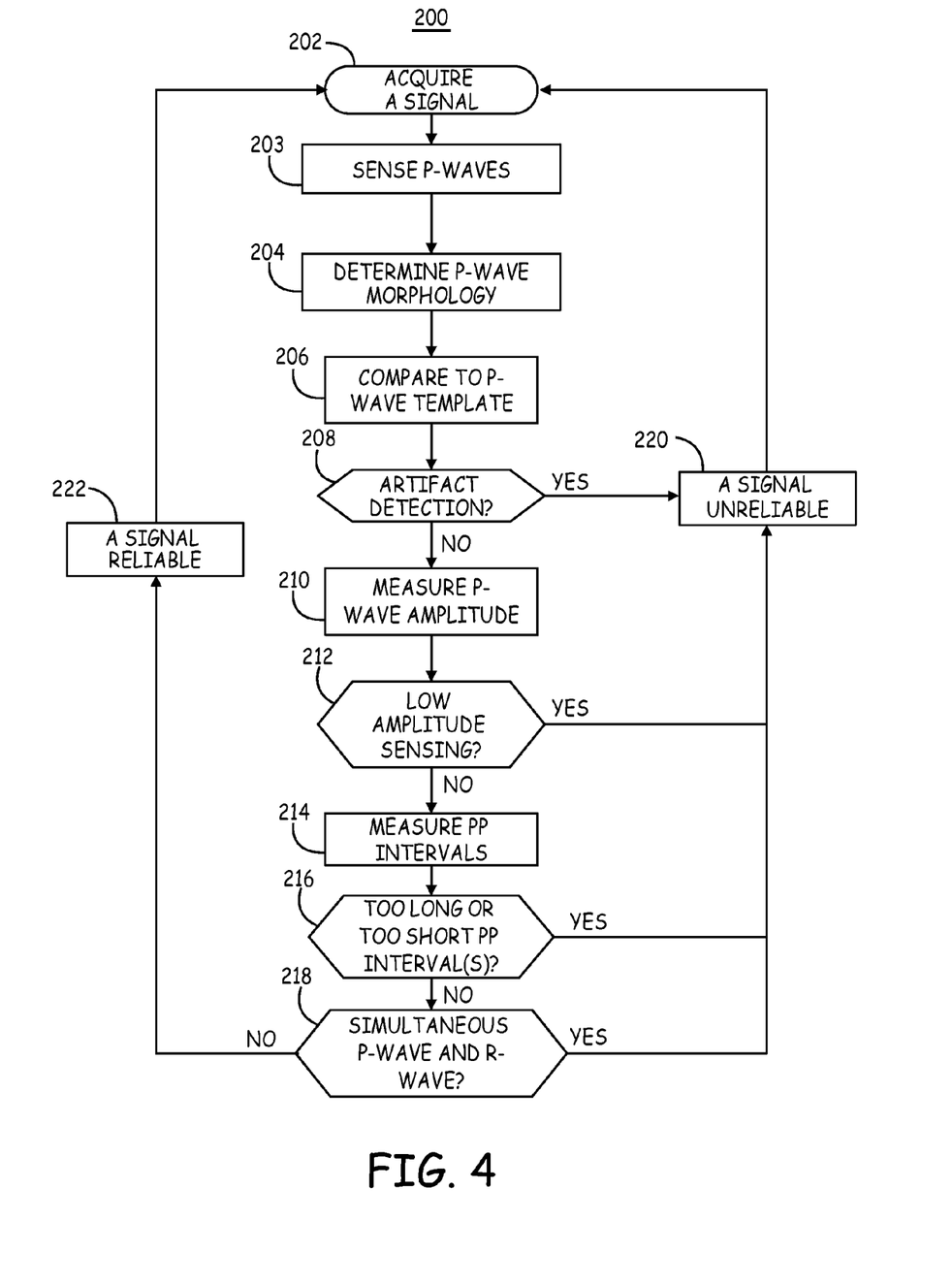
FIG. 4 is a flow chart of a method for determining whether an atrial signal is unreliable according to one embodiment.

FIG. 4 is a flow chart 200 of a method for determining whether an atrial signal is unreliable according to one embodiment. In one embodiment, an atrial signal is determined to be unreliable if the signal is suspected to contain non-cardiac signal artifact, undersensing of P-waves, oversensing of far-field R-waves, oversensing of noise or artifacts, or evidence of lead dislodgement. In various embodiments, evidence of any one of these indicators of an unreliable signal may be used to disable the use of atrial information for cardiac event detection. In general, P-wave morphology analysis, P-wave signal amplitude relative to a sensing threshold, intervals between consecutively sensed P-waves (i.e. PP intervals), and intervals between consecutively sensed P-waves and R-waves (PR or RP intervals), individually or any combination thereof, may be used in analyzing the atrial signal for determining whether it is reliable. In the embodiment shown in FIG. 4, P-wave morphology is used for detecting noise or signal artifact; P-wave amplitude and PP intervals are used for detecting possible P-wave undersensing, and PR (or RP) intervals are used for detecting possible lead dislodgment. The analysis of the atrial signal for detecting undersensing, oversensing and/or lead-related issues as indicators of an unreliable atrial signal may use morphology and timing-related signal features, alone or in combination.

In the illustrative embodiment shown in FIG. 4, beginning at block 202, the atrial signal is acquired. P-waves are sensed from the atrial signal at block 203. A morphology measurement is determined at block 204 from one or more sensed P-waves for use in detecting non-cardiac artifact. The morphology measurement may be one or more measurements of a specific time-based or magnitude-based P-wave feature. Specific P-wave morphology feature measurements may include any of a peak amplitude, maximum or minimum slope, P-wave width, or time of a P-wave feature relative to a fiducial point such the time of a P-wave peak amplitude or peak slope relative to a sensing threshold crossing or a zero-crossing. Additionally or alternatively, the P-wave morphology measurement determined at block 204 may be a digitized overall P-wave morphology used in a morphology analysis that includes an overall morphology template comparison for computing a morphology matching score, which may include a wavelet analysis. A wavelet morphology analysis method is generally described in U.S. Pat. No. 6,393,316 (Gillberg, et al.), hereby incorporated herein by reference in its entirety.

At block 206, the P-wave morphology measurement is compared to a P-wave template, which may be a threshold range of a specific P-wave feature measurement or an overall P-wave morphology-matching score threshold, or combination thereof. Based on this comparison, non-cardiac artifact may be detected at block 208. If artifact is detected, the atrial signal is determined to be unreliable at block 220.

If signal artifact is not detected at block 208, the P-wave amplitude may be measured at block 210 to determine if P-wave undersensing is likely. The P-wave amplitude measurement (which may be a single maximum P-wave amplitude or combination of maximum amplitudes from multiple P-waves) is compared to the sensing threshold at block 212. If P-waves are being sensed within a predetermined, small range of the sensing threshold (e.g., within 100% to 150% of the sensing threshold), or right at the sensing threshold, this low amplitude P-wave sensing may indicate that some P-waves, or future P-waves, are likely to be undersensed. This possibility of undersensing of low amplitude P-waves relative to a sensing threshold is used as an indicator of an unreliable atrial signal, and that determination is made at block 220.

Additionally or alternatively, PP intervals may be measured at block 214 to detect possible oversensing or undersensing of P-waves. If one or more long PP intervals are detected at block 216, the long interval(s) are an indicator of possible P-wave undersensing. The atrial signal is determined to be unreliable at block 220. A PP interval may be detected as a "long" interval when it is greater than one or more preceding PP intervals by more than a predetermined fixed threshold or percentage difference. In one embodiment, a PP interval or some combination of PP intervals that is/are approximately 50% to 120% longer than a preceding PP interval is detected as a long interval and may be used as an indicator of possible P-wave undersensing in the determination of whether the atrial signal is unreliable. In some embodiments, an absolute time interval threshold, for example approximately 2 seconds, may be applied for detecting a long PP interval. Alternatively, if one or more of the P-P intervals are found to be very short (such as <110 ms) at decision block 216, this may serve as an indicator that the atrial signal is unreliable (block 220).

At decision block 218, PR or RP intervals are measured to detect simultaneous P-wave and R-wave sensed events. This situation may reflect dislodgement of the atrial lead into the ventricle; thus, activity sensed by the atrial lead actually reflects ventricular activity, not atrial activity. Simultaneous sensed events may be defined to be a P-wave and an R-wave sensed within a narrow time interval of each other, e.g. a time interval of approximately 30 ms or less. Simultaneous sensed "P-waves" and "R-waves" indicate possible atrial lead dislodgment into the ventricular chamber. If P- and R-waves are sensed simultaneously, i.e. without an atrial-ventricular delay there between, the atrial signal is determined to be unreliable at block 220.

The situation of nearly simultaneous P-wave and R-wave sensing can also be present with some cardiac rhythms like AV nodal reentrant tachycardia (AVNRT). To discriminate lead dislodgement from AVNRT, the decision block 218 may include delivering an atrial or ventricular pace prematurely when P-wave and R-wave sensing is occurring substantially simultaneously. If an event is sensed in the non-paced chamber nearly simultaneously with the pacing pulse, this simultaneous pace/sense in the two chambers is evidence of lead dislodgement. Alternatively, a short burst of pacing in either the atrium or the ventricle may be delivered while observing sensing in the other chamber. Sensing in one chamber coincident with pacing in the other chamber is used to confirm lead dislodgement. In other embodiments, if an intrinsic premature ventricular contraction (PVC) occurs as evidenced by a short coupling interval followed by a long pause or other PVC detection methods, and an atrial P-wave occurs simultaneously with the PVC detection, this is also strong evidence for atrial lead dislodgement.

If one or more required criteria for detecting an unreliable atrial signal are met at decision blocks 208, 212, 216 or 218, switching to a ventricular-only cardiac event detection algorithm is performed as described in conjunction with FIG. 3. It is recognized that detection of an unreliable atrial signal may require a single atrial cycle or multiple atrial cycles depending on how the one or more criterion for detecting an unreliable atrial signal are defined. While multiple criteria are illustrated in FIG. 4, with any one satisfied criterion resulting in detecting an unreliable signal, it is contemplated that a single criterion may be applied for detecting an unreliable signal. Furthermore, multiple criteria may be required to be satisfied, or the same criterion may be required to be satisfied for more than one atrial cycle, in order to detect an unreliable atrial signal.

If criteria required for detecting an unreliable signal are not met, the control processor of the IMD continues to use both the atrial and ventricular signals for cardiac event detection (or restore a detection mode requiring the use of both atrial and ventricular signals if the use of an unreliable atrial signal had previously been disabled).

In other embodiments, another physiological signal correlated to cyclical atrial function may be used at block 104 of FIG. 3 to determine if the atrial signal is unreliable. For example, an atrial pressure signal and an atrial electrical signal may be sensed and atrial activations may be identified based on respective threshold crossings. If a 1:1 correspondence exists between atrial activations detected from an atrial electrical signal and atrial activations detected from an atrial pressure signal, or other secondary signal, the atrial electrical signal is confirmed as being reliable. If a 1:1 correspondence does not exist between two different atrial signals, at least one of the atrial signals is determined to be unreliable.

Figure 5:
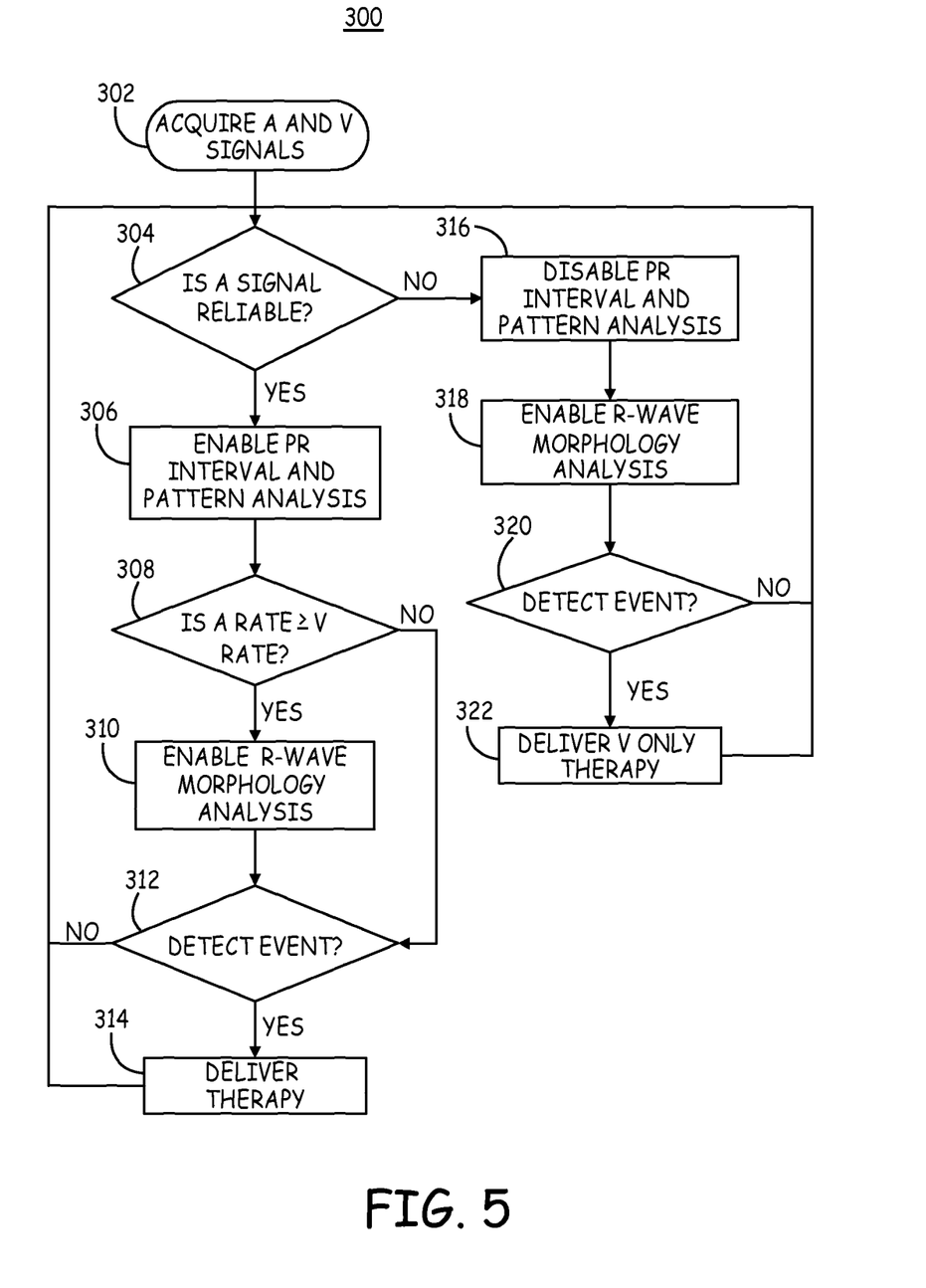
FIG. 5 is a flow chart of a method for controlling cardiac arrhythmia detection in an IMD according to an alternative embodiment.

FIG. 5 is a flow chart 300 of a method for controlling cardiac event detection in an IMD according to one embodiment. As previously described herein, atrial and ventricular signals are acquired at block 302, and the atrial signal is monitored at block 304 to determine if the atrial signal becomes unreliable. As long as the atrial signal is reliable, a cardiac event detection algorithm relying on both the atrial and ventricular signals is enabled and operating.

In one illustrative embodiment, PR intervals (and/or RP intervals) and/or patterns of sensed P-waves and R-waves are used to discriminate SVT from VT/VF. An arrhythmia discrimination algorithm using PR intervals and PR pattern analysis is generally described in U.S. Pat. No. 6,487,443 (Olson, et al.), hereby incorporated herein by reference in its entirety. The PR intervals and pattern analysis remains enabled (or is re-enabled if previously disabled due to an unreliable atrial signal) at block 306.

In one particular cardiac rhythm discrimination algorithm, the atrial rate is used to trigger an R-wave morphology analysis for discriminating between SVT and VT/VF. For example, a wavelet morphology analysis is enabled (as indicated at block 310) when a fast ventricular rate is detected indicating a possible VT or VF, and the atrial rate is greater than or equal to (within a predetermined range) the ventricular rate (as determined at block 308). Stated differently, a ventricular rate that is not substantially greater than an atrial rate is evaluated further using a morphology analysis. If the ventricular rate is substantially greater than the atrial rate, the morphology analysis is not necessary to discriminate the fast ventricular rate as being ventricular in origin.

If a cardiac event requiring therapy is detected using both the atrial and ventricular signal at block 312, a therapy is delivered according to a programmed menu of therapies at block 314. The process then returns to block 304 to continue monitoring the atrial signal.

If the atrial signal is determined to be unreliable at decision block 304, the use of any relationship between atrial activations and ventricular activations, e.g. PR interval and PR pattern analysis, is disabled at block 316. R-wave morphology analysis is enabled at block 318 for use in combination with RR interval measurements for detecting a cardiac event. Morphology analysis or other algorithm components may normally be enabled or triggered in response to atrial information, such as the atrial rate requirement indicated at block 308 for enabling R-wave morphology analysis. In the embodiment shown, discrimination algorithm components that are normally enabled in response to triggering atrial information are automatically enabled when atrial information is unreliable. In other words, detection algorithm components may be enabled without applying atrial conditions as pre-requisites for performing additional algorithm components. When the use of atrial information is disabled due to an unreliable atrial signal (block 304), R-wave morphology analysis is enabled at block 318, without requiring an atrial condition to be met. R-wave morphology may be performed on a beat-by-beat basis or may be triggered when a fast ventricular rate is detected without the requirement of the atrial rate exceeding the ventricular rate.

If a cardiac event, which requires therapy, is detected at block 320, a therapy is delivered at block 322. The therapy may be limited to be a ventricular-only therapy when the atrial signal is unreliable. If no event is detected, or if a therapy is delivered, the process returns to block 304 to continue monitoring the atrial signal.

Figure 6:
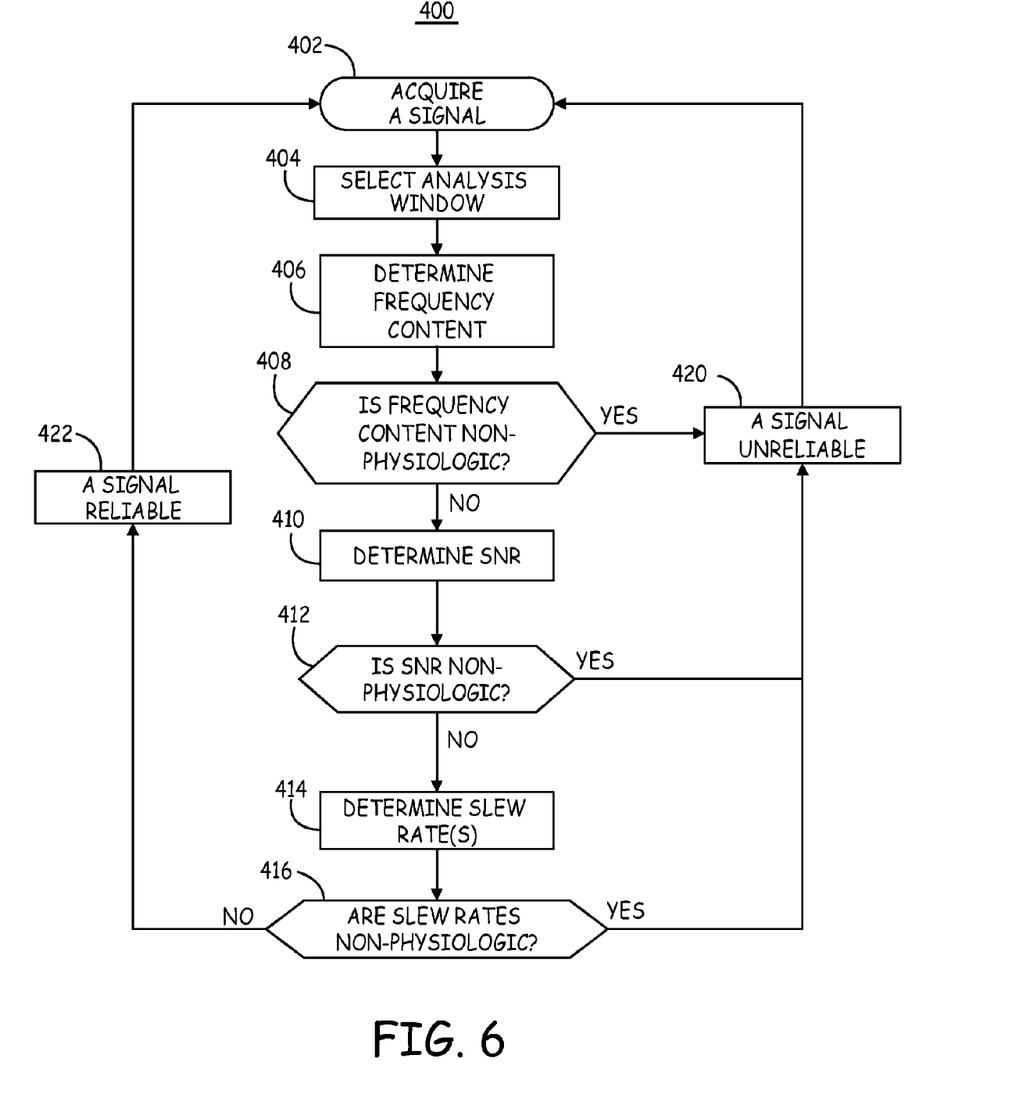
FIG. 6 is a flow chart of a method for determining whether an atrial signal is reliable according to an alternative embodiment.

FIG. 6 is a flow chart 400 of a method for determining whether an atrial signal is reliable according to an alternative embodiment. The method shown in FIG. 6 may be used alone or in combination with any of the criteria for determining an unreliable signal shown in FIG. 4. Generally, the method shown in FIG. 6 does not rely on sensing atrial activations (e.g. P-waves) from an acquired atrial signal. Instead, an atrial signal is acquired at block 402 and an atrial signal segment over a predetermined analysis time window is sampled at block 404. The signal segment is obtained independent of sensed atrial P-waves. Morphology-related analysis is performed over the entire time window without requiring detection of P-waves during the time window. For example, the atrial signal is digitized and sampled over a one-second, two-second or other predetermined analysis window at bock 404.

One or more morphology-related metrics are determined for detecting non-physiological (i.e. non-atrial) signal content. Several examples of morphology-related metrics are described in the following in conjunction with flow chart 400. It is recognized that these metrics may be used alone or in any combination for determining if the atrial signal is unreliable based on evidence of non-physiological signal content. Furthermore, it is recognized that other morphology metrics computed using the atrial signal acquired over an analysis time window may be used in addition or alternatively to the illustrative morphology metrics described here.

One aspect of the signal morphology that may provide evidence of non-physiological signal content is frequency information. At block 406, a frequency analysis is performed to determine the frequency content of the signal during the analysis window. For example, a frequency power spectrum, a maximum frequency, median or mean frequency, or presence of 50/60 Hz line frequency may be determined at block 406.

At block 408, a metric of the frequency content is compared to a threshold for detecting non-physiological frequency content. If a frequency metric is determined to exceed a physiological frequency threshold or range, the signal is considered to contain non-physiological noise and the atrial signal is determined to be unreliable at block 420.

Additionally or alternatively, a signal-to-noise ratio (SNR) may be determined at block 410. Determination of a SNR may involve peak detection algorithms with a comparison of one or more peak amplitudes within the analysis window to a signal amplitude determined between peaks. In one embodiment, a high fixed sensing threshold is applied and progressively lowered until a reasonable number and density of peaks within the analysis window is found. The reasonable or acceptable peak number and density will depend in part on the duration of the analysis window. For example, a 2-second window may require at least 2 signal peaks being detected and spaced apart by at least 500 ms.

Alternatively, a relative energy of signal in a high frequency band (e.g., >15-20 Hz) could be compared to the energy in a low frequency band (e.g., <15-20 Hz). The ratio of these bands is analogous to a SNR. If the ratio is high, the SNR is poor; if the ratio is low, the SNR is good.

If the SNR is too low or outside an established physiological range, the signal is determined to contain non-physiological content at block 412. The atrial signal is determined to be unreliable at block 420.

Other signal amplitude related metrics may be determined at block 410 for detecting non-physiological signal content at decision block 412. For example, a maximum, average or other measurement of signal amplitude may be determined during the analysis window. The signal amplitude may be found to exceed an expected physiological maximum (for example when signal clipping occurs) or found to be too small to be reliable.

Additionally or alternatively, one or more measurements of slew rate during the analysis window are determined at block 414. Slew rates falling outside an expected physiological range, (block 416) may indicate an unreliable atrial signal (block 420). In other words, slew rates greater than a maximum physiological slew rate threshold and/or less than a minimum physiological slew rate threshold may indicate the signal includes non-physiological content.

If the metrics determined for the atrial signal over an analysis window are not found to contain non-physiological frequency content, amplitude content, and/or slew rate content, the atrial signal is determined to be reliable at block 422. The atrial signal is used for cardiac rhythm detection and discrimination algorithms as described above. If the atrial signal is found unreliable, the IMD switches an arrhythmia detection mode to eliminate or ignore the use of atrial signal information.

While illustrative embodiments described herein relate to switching a cardiac event detection mode of operation in response to determining that an atrial signal is unreliable, it is contemplated that such switching may occur in response to detecting that a ventricular signal is unreliable such that only an atrial signal is used for detecting cardiac events and ventricular information is ignored.

Furthermore, while flow charts presented herein depict a particular order or sequence of signal analyses and decisions relating to whether an atrial signal is reliable, it is recognized that the analysis and decision blocks may be performed in a different order or in other combinations or subsets than the illustrative embodiments described herein and still provide a determination of whether a cardiac signal is reliable.

Thus, an IMD and associated methods for controlling cardiac event detection have been presented in the foregoing description with reference to specific embodiments. It is appreciated that various modifications to the referenced embodiments may be made without departing from the scope of the disclosure as set forth in the following claims.

The invention claimed is:

1. A method for use in an implantable medical device for detecting cardiac arrhythmias in a patient, the method comprising:
    acquiring a first cardiac signal in a first heart chamber, the first cardiac signal comprising events corresponding to activations of the first heart chamber;
    acquiring a second cardiac signal in a second heart chamber, the second cardiac signal comprising events corresponding to activations of the second heart chamber;
    determining whether the first signal is unreliable; and
    switching from a first cardiac arrhythmia detection mode of operation to a second cardiac arrhythmia detection mode of operation in response to determining the first signal to be unreliable, the first detection mode corresponding to using both the first cardiac signal and the second cardiac signal, and the second detection mode corresponding to using the second cardiac signal and not the first cardiac signal.

2. The method of claim 1, wherein determining whether the first cardiac signal is unreliable comprises:
    determining a morphology of the first signal; and
    detecting signal artifact in response to the determined morphology.

3. The method of claim 1, wherein determining whether the first cardiac signal is unreliable comprises:
    determining an amplitude of the first cardiac signal;
    comparing the determined amplitude to a sensing threshold; and
    determining whether the first cardiac signal corresponds to a low amplitude signal in response to the comparing.

4. The method of claim 1, wherein determining whether the first cardiac signal is unreliable comprises:
    determining a time interval between activations of the first heart chamber;
    comparing the determined time interval to a long pause threshold; and
    determining undersensing of the activations in response to the comparing.

5. The method of claim 1, wherein determining whether the first cardiac signal is unreliable comprises determining whether activations sensed from the first cardiac signal occur simultaneously with activations sensed from the second cardiac signal.

6. The method of claim 1, wherein the first cardiac arrhythmia detection mode comprises determining a relation between activations sensed from the first cardiac signal and activations sensed from the second cardiac signal, and wherein switching from the first mode to the second mode comprises disabling determining the relation between activations sensed from the first cardiac signal and activations sensed from the second cardiac signal.

7. The method of claim 1, wherein the first cardiac event detection mode comprises:
    determining a first rate of activations sensed from the first cardiac signal;
    comparing the first rate to a second rate of activations sensed from the second cardiac signal; and
    enabling a morphology analysis of the second cardiac signal in response to the comparing, wherein switching from the first mode to the second mode comprises:
    disabling determining the first rate of activations sensed from the first cardiac signal and the comparing; and
    enabling the morphology analysis of the second cardiac signal.

8. The method of claim 1, further comprising:
    monitoring the first cardiac signal, in response to determining the first cardiac signal is unreliable, to determine whether the first cardiac signal is no longer unreliable; and
    switching from the second cardiac arrhythmia detection mode to the first cardiac arrhythmia detection mode in response to determining the first cardiac signal is no longer unreliable.

9. The method of claim 1, further comprising disabling therapy delivery in the first cardiac chamber in response to switching to the second arrhythmia detection mode of operation.

10. The method of claim 1, wherein the first cardiac signal is an atrial electrical signal and the second cardiac signal is a ventricular electrical signal.

11. The method of claim 1, wherein determining whether the first signal is unreliable comprises analyzing the first signal to determine an indicator of whether the first signal is unreliable for use in cardiac arrhythmia detection.

12. An implantable medical device for detecting cardiac arrhythmias in a patient, comprising:
    a first sensor to acquire a first cardiac signal in a first heart chamber, the first cardiac signal comprising events corresponding to activations of the first heart chamber;
    a second sensor to acquire a second cardiac signal in a second heart chamber, the second cardiac signal comprising events corresponding to activations of the second heart chamber;
    a processor configured to receive the first and second cardiac signals and to determine whether the first cardiac signal is unreliable, switch from a first cardiac arrhythmia detection mode of operation to a second cardiac arrhythmia detection mode of operation in response to determining the first signal to be unreliable, the first detection mode corresponding to using both the first cardiac signal and the second cardiac signal, and the second detection mode corresponding to using the second cardiac signal and not the first cardiac signal.

13. The device of claim 12, wherein determining whether the first cardiac signal is unreliable comprises:
    determining a morphology of the first signal; and
    detecting signal artifact in response to the determined morphology.

14. The device of claim 12, wherein determining whether the first cardiac signal is unreliable comprises:
    determining an amplitude of the first cardiac signal;
    comparing the determined amplitude to a sensing threshold; and
    determining whether the first cardiac signal corresponds to a low amplitude signal in response to the comparing.

15. The device of claim 12, wherein determining whether the first cardiac signal is unreliable comprises:
    determining a time interval between activations of the first heart chamber;
    comparing the determined time interval to a long pause threshold; and determining undersensing of the activations in response to the comparing.

16. The device of claim 12, wherein determining whether the first cardiac signal is unreliable comprises determining whether activations sensed from the first cardiac signal occur simultaneously with activations sensed from the second cardiac signal.

17. The device of claim 12, wherein the first cardiac arrhythmia detection mode comprises determining a relation between activations sensed from the first cardiac signal and activations sensed from the second cardiac signal and wherein switching from the first mode to the second mode comprises disabling determining the relation between activations sensed from the first cardiac signal and activations sensed from the second cardiac signal.

18. The device of claim 12, wherein the first cardiac event detection mode comprises:
   determining a first rate of activations sensed from the first cardiac signal;
   comparing the first rate to a second rate of activations sensed from the second cardiac signal; and
   enabling a morphology analysis of the second cardiac signal in response to the comparing, and wherein switching from the first mode to the second mode comprises:
   disabling determining the first rate of activations sensed from the first cardiac signals and the comparing; and
   enabling the morphology analysis of second cardiac signal.

19. The device of claim 12, wherein the processor is further configured to monitor the first cardiac signal, in response to determining the first cardiac signal is unreliable, to determine whether the first cardiac signal is no longer unreliable, and switch from the second cardiac arrhythmia detection mode to the first cardiac arrhythmia detection mode in response to determining the first cardiac signal is no longer unreliable.

20. The device of claim 12, further comprising a therapy delivery circuit to deliver a therapy in response to detecting a cardiac arrhythmia, wherein the processor is configured to disable therapy delivery in the first cardiac chamber in response to switching to the second arrhythmia detection mode of operation.

21. A non-transitory computer-readable medium storing a set of instructions in an implantable medical device for performing a method comprising:
   acquiring a first cardiac signal in a first heart chamber, the first cardiac signal comprising events corresponding to activations of the first heart chamber;
   acquiring a second cardiac signal in a second heart chamber, the second cardiac signal comprising events corresponding to activations of the second heart chamber;
   determining whether the first signal is unreliable; and
   switching from a first cardiac arrhythmia detection mode of operation to a second cardiac arrhythmia detection mode of operation in response to determining the first signal to be unreliable, the first detection mode corresponding to using both the first cardiac signal and the second cardiac signal, and the second detection mode corresponding to using the second cardiac signal and not the first cardiac signal.

* * * * *